US009244025B2

(12) United States Patent
Ohgarane et al.

(10) Patent No.: US 9,244,025 B2
(45) Date of Patent: Jan. 26, 2016

(54) TRANSMISSION ELECTRON DIFFRACTION MEASUREMENT APPARATUS AND METHOD FOR MEASURING TRANSMISSION ELECTRON DIFFRACTION PATTERN

(71) Applicant: Semiconductor Energy Laboratory Co., Ltd., Atsugi-shi, Kanagawa-ken (JP)

(72) Inventors: Daisuke Ohgarane, Hadano (JP); Koji Dairiki, Atsugi (JP); Masahiro Takahashi, Atsugi (JP); Shunichi Ito, Atsugi (JP); Erika Takahashi, Atsugi (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 14/305,173

(22) Filed: Jun. 16, 2014

(65) Prior Publication Data
US 2015/0008321 A1 Jan. 8, 2015

(30) Foreign Application Priority Data

Jul. 5, 2013 (JP) .................. 2013-141217

(51) Int. Cl.
*G01N 23/205* (2006.01)
*G01N 23/20* (2006.01)
*H01J 37/06* (2006.01)

(52) U.S. Cl.
CPC ...... *G01N 23/2055* (2013.01); *G01N 23/20058* (2013.01); *H01J 37/06* (2013.01); *G01N 2223/61* (2013.01)

(58) Field of Classification Search
USPC ............. 250/306–311, 359.1, 360.1, 492.3, 250/442.11
See application file for complete search history.

(56) References Cited

U.S. PATENT DOCUMENTS

| 5,140,352 | A | * | 8/1992 | Moore et al. ............... 348/78 |
| 5,898,177 | A | * | 4/1999 | Hidaka ............... H01J 37/20 250/311 |
| 6,061,085 | A | | 5/2000 | Daberkow et al. |
| 6,531,697 | B1 | | 3/2003 | Nakamura et al. |
| 7,227,144 | B2 | | 6/2007 | Tsuneta et al. |
| 7,372,029 | B2 | | 5/2008 | Tsuneta et al. |

(Continued)

FOREIGN PATENT DOCUMENTS

JP  2006-165528 A  6/2006

OTHER PUBLICATIONS

Kimizuka.N et al., "Syntheses and Single-Crystal Data of Homologous Compounds, In2O3(ZnO)m (m=3, 4, and 5). InGaO3(ZnO)3, and Ga2O3(ZnO)m (m=7, 8, 9, and 16) in the In2O3—ZnGa2O4—ZnO System", Journal of Solid State Chemistry, Apr. 1, 1995, vol. 116, No. pp. 170-178.

(Continued)

*Primary Examiner* — Bernard E Souw
(74) *Attorney, Agent, or Firm* — Robinson Intellectual Property Law Office; Eric J. Robinson

(57) ABSTRACT

Provided is a transmission electron diffraction measurement apparatus including an electron gun; a first optical system under the electron gun; a sample chamber under the first optical system; a second optical system under the sample chamber; an observation chamber under the second optical system; a region that emits light by receiving energy from an electron in the observation chamber; and a camera facing the region.

18 Claims, 13 Drawing Sheets

(56) References Cited

U.S. PATENT DOCUMENTS

| | | | |
|---|---|---|---|
| 7,601,956 B2 * | 10/2009 | Sergeevich | H01J 37/295 250/310 |
| 7,791,072 B2 | 9/2010 | Kumomi et al. | |
| 8,237,166 B2 | 8/2012 | Kumomi et al. | |
| 2004/0150714 A1 * | 8/2004 | Lin | 348/126 |
| 2005/0195365 A1 * | 9/2005 | Lamarre | H04N 5/222 352/47 |
| 2006/0076492 A1 * | 4/2006 | Taniguchi et al. | 250/311 |
| 2008/0093565 A1 * | 4/2008 | Yaguchi et al. | 250/440.11 |
| 2009/0159797 A1 * | 6/2009 | Fukushima | H01J 37/09 250/311 |
| 2010/0091101 A1 * | 4/2010 | Fujimoto et al. | 348/79 |
| 2010/0238238 A1 * | 9/2010 | Yamamoto | B41J 2/1404 347/85 |
| 2011/0292385 A1 * | 12/2011 | Haustein et al. | 356/302 |
| 2014/0124776 A1 * | 5/2014 | Takahashi | C23C 14/086 257/43 |
| 2014/0239294 A1 * | 8/2014 | Yamazaki | H01L 29/7869 257/43 |
| 2014/0264017 A1 * | 9/2014 | Nakazawa et al. | 250/307 |

OTHER PUBLICATIONS

Kimizuka. N et al., "Spinel,YBFE2O4, and YB2FE3O7 Types of Structures for Compounds in the In2O3 and Sc2O3—A2O3—Bo Systems [A; Fe, Ga, or Al; B: Mg, Mn, Fe, Ni, Cu, or Zn] at Temperatures over 1000° C.", Journal of Solid State Chemistry, 1985, vol. 60, pp. 382-384.

Yamazaki.S et al., "Research, Development, and Application of Cyrstaline Oxide Semiconductor", SID Digest '12: SID International Symposium Digest of Technical Papers, Jun. 5, 2012, pp. 183-186.

* cited by examiner

FIG. 1A
FIG. 1B
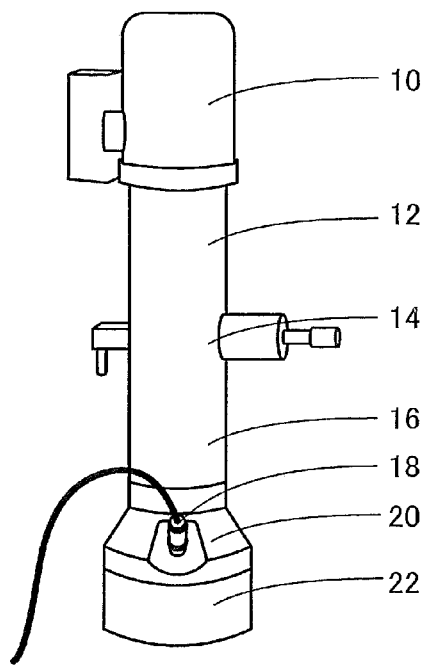
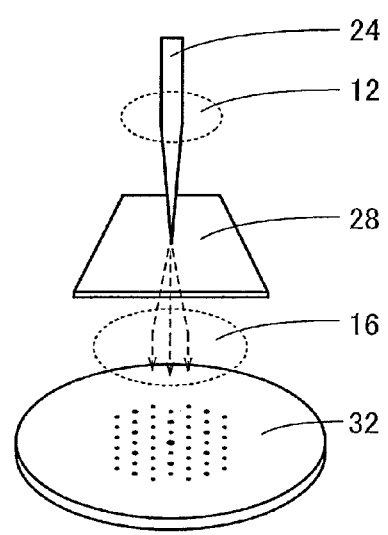

FIG. 4A1
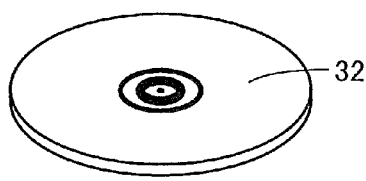
FIG. 4A2
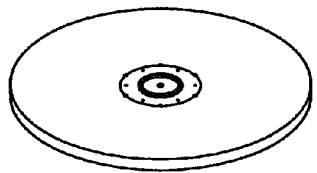
FIG. 4A3
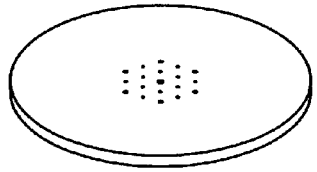
FIG. 4B
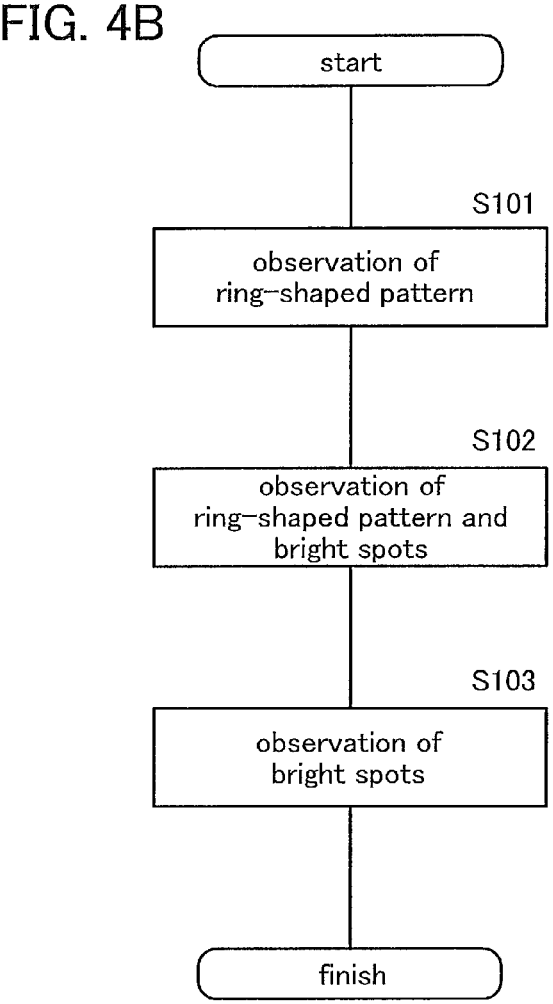

FIG. 5A1
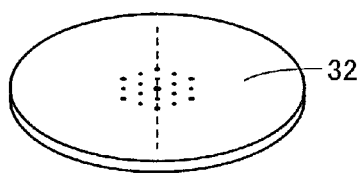
FIG. 5A2
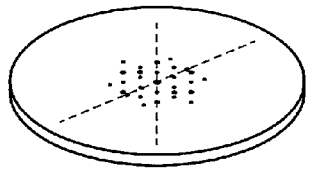
FIG. 5A3
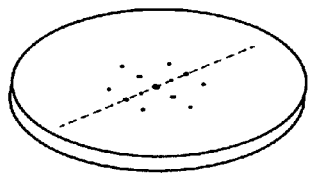
FIG. 5B
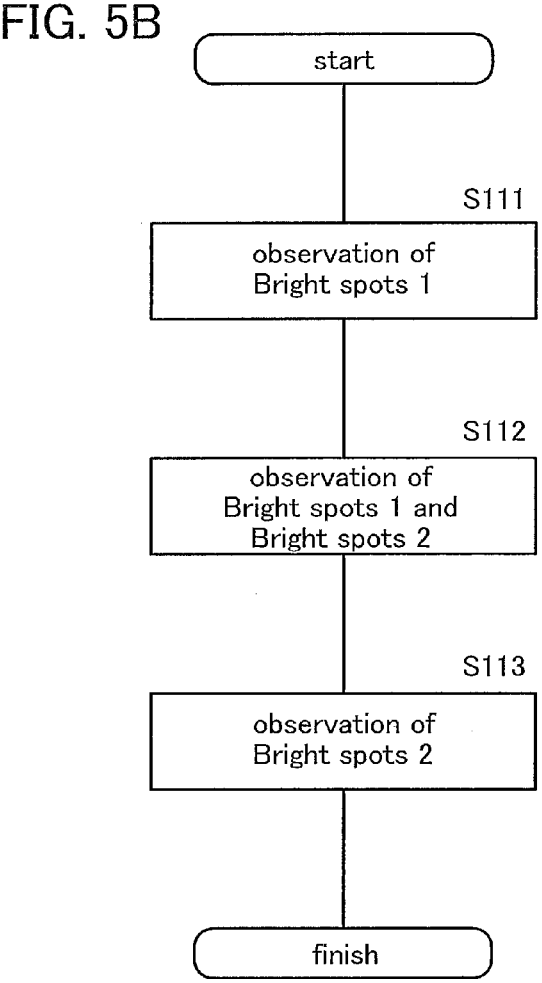

FIG. 6A1
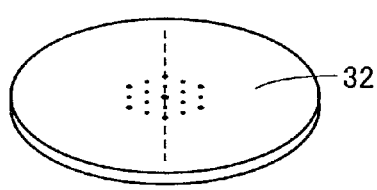
FIG. 6B
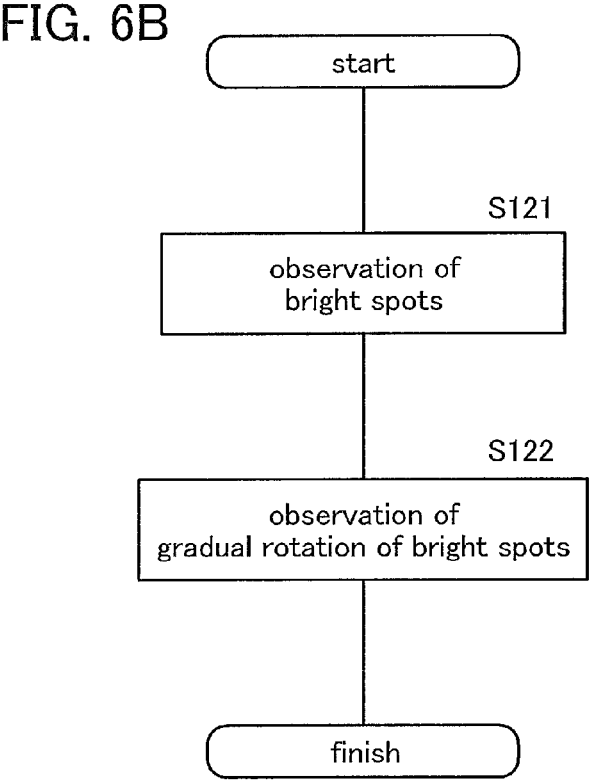
FIG. 6A2
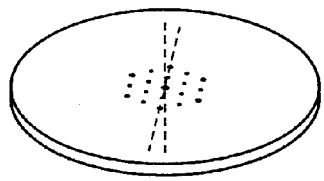
FIG. 6A3
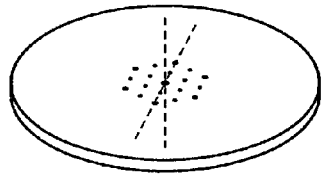

FIG. 7A1
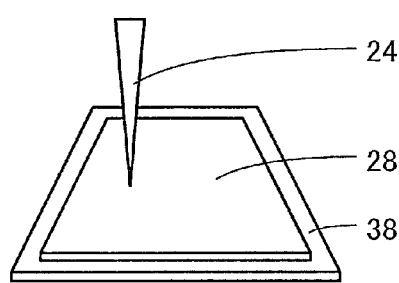
FIG. 7A2
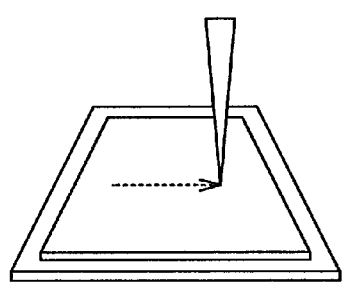
FIG. 7B
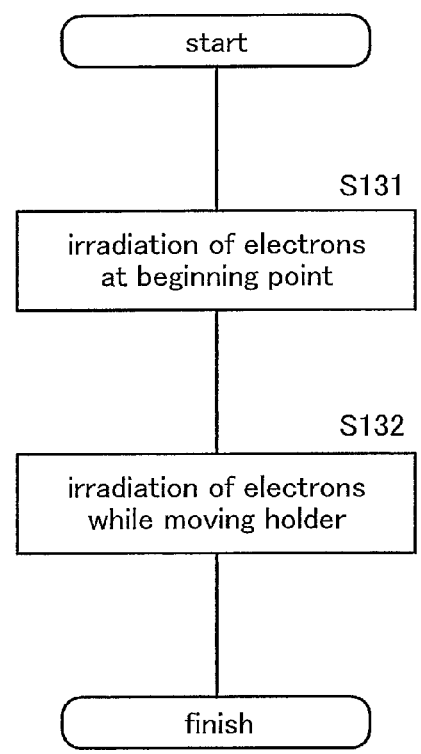

FIG. 8A1
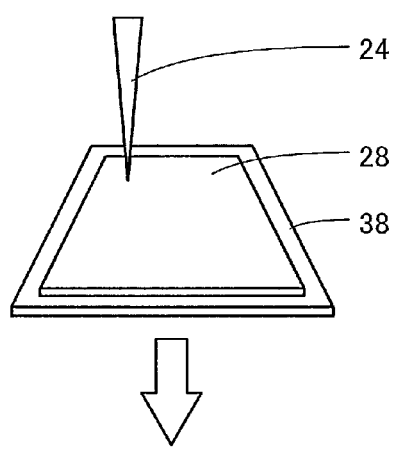
FIG. 8A2
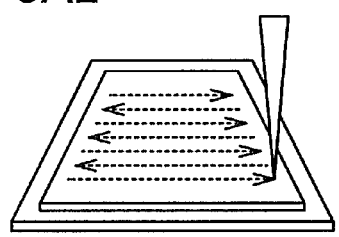
FIG. 8A3
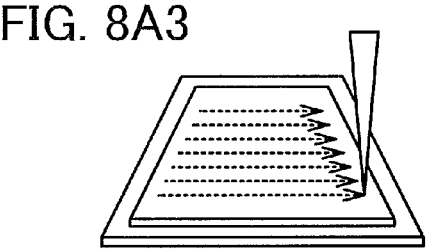
FIG. 8B
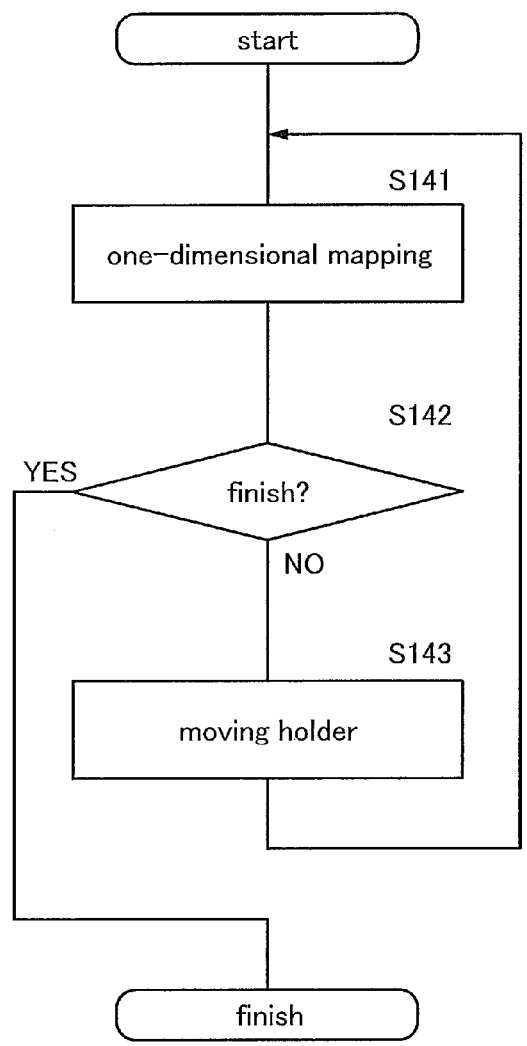

FIG. 9A1
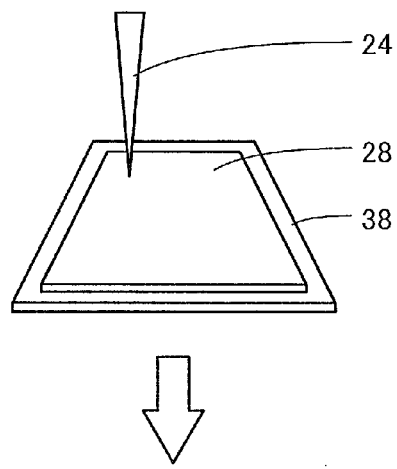
FIG. 9A2
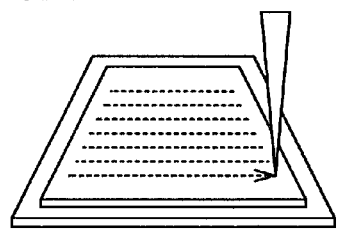
FIG. 9B
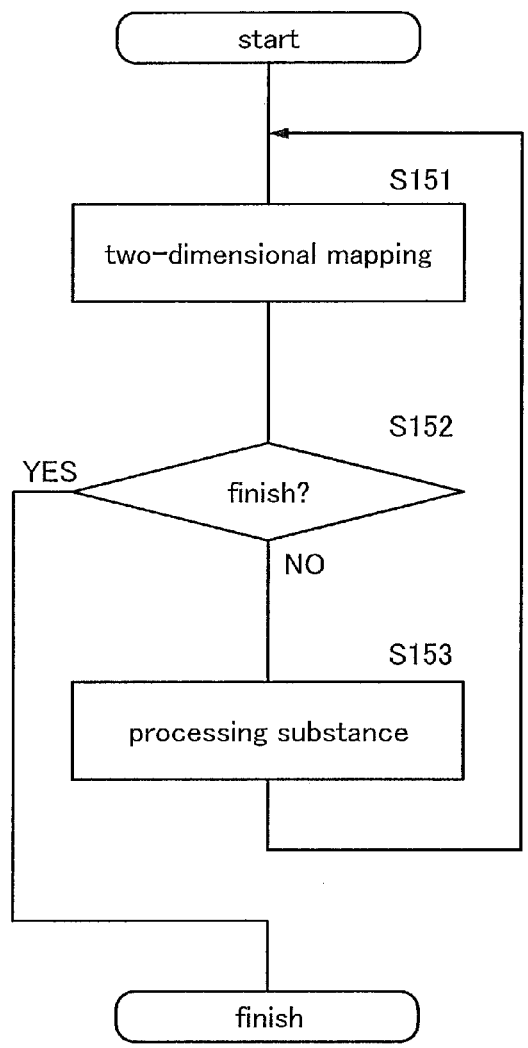

TRANSMISSION ELECTRON DIFFRACTION MEASUREMENT APPARATUS AND METHOD FOR MEASURING TRANSMISSION ELECTRON DIFFRACTION PATTERN

BACKGROUND OF THE INVENTION

1. Field of the Invention

The present invention relates to a transmission electron diffraction measurement apparatus and a method for measuring a transmission electron diffraction pattern. In particular, the present invention relates to a method for measuring change in a transmission electron diffraction pattern of a substance.

2. Description of the Related Art

In recent years, an oxide semiconductor film has attracted attention. For example, a transistor which includes an amorphous In—Ga—Zn oxide film is disclosed (see Patent Document 1). An oxide semiconductor film can be formed by a sputtering method or the like, and thus can be used for a semiconductor film of a transistor in a large display device. Moreover, a transistor including an oxide semiconductor film has a high field-effect mobility; therefore, a high-performance display device where driver circuits are formed over the same substrate can be obtained. In addition, there is an advantage that capital investment can be reduced because part of production equipment for a transistor including an amorphous silicon film can be retrofitted and utilized.

Synthesis of a single crystal In—Ga—Zn oxide is reported in 1985 (see Non-Patent Document 1). Furthermore, it is reported that an In—Ga—Zn oxide has a homologous structure and is represented by a composition formula, $InGaO_3(ZnO)_m$ (m is a natural number) (see Non-Patent Document 2).

A transistor which includes a crystalline In—Ga—Zn oxide film and has excellent electrical characteristics and reliability as compared to a transistor including an amorphous In—Ga—Zn oxide film is reported (see Non-Patent Document 3). Non-Patent Document 3 reports that a clear crystal grain boundary is not observed in an In—Ga—Zn oxide film including a c-axis aligned crystal (CAAC).

It is known that a crystal grain boundary in a semiconductor film adversely affects the electrical characteristics of a. transistor. There is a possibility that a crystal structure in which a crystal grain boundary is not clearly observed, such as an In—Ga—Zn oxide film including CAAC, is a novel crystal structure.

REFERENCE

Patent Document

[Patent Document 1]Japanese Published Patent Application No. 2006-165528

Non-Patent Document

[Non-Patent Document 1]N. Kimizuka and T. Mohri, "Spinel, $YbFe_2O_4$, and $Yb_2Fe_3O_7$ Types of Structures for Compounds in the $In_2O_3$ and $Sc_2O_3$-$A_2O_3$—BO Systems [A: Fe, Ga, or Al; B: Mg, Mn, Fe, Ni, Cu, or Zn] at Temperatures over 1000° C.", *J. Solid State Chem.,* 1985, Vol. 60, pp. 382-384

[Non-Patent Document 2]N. Kimizuka., M. Isobe, and M. Nakamura, "Syntheses and Single-Crystal Data of Homologous Compounds, $In_2O_3(ZnO)_m$ (m=3, 4, and 5), $InGaO_3(ZnO)_3$, and $Ga_2O_3(ZnO)_m$, (m=7, 8, 9, and 16) in the $In_2O_3$—$ZnGa_2O_4$—ZnO System", *J. Solid State Chem.,* 1995, Vol. 116, pp. 170-178

[Non-Patent Document 3]S. Yamazaki, J. Koyama, Y. Yamamoto, and K. Okamoto, "Research, Development, and Application of Crystalline Oxide Semiconductor", *SID 2012 DIGEST,* p. 183-186

SUMMARY OF THE INVENTION

An analysis method focusing on a structure between crystal regions has been far from established. In particular, in the case where the size of a crystal region is several nanometers to several tens of nanometers, there is a limited number of methods for analyzing the structure between crystal regions.

For example, a transmission electron diffraction measurement apparatus can be used to analyze the structure of a substance including minute crystal regions.

However, a conventional transmission electron diffraction measurement apparatus employs a mode in which a film chamber is located just under an observation chamber, a film or an imaging plate is used as a medium for photographing, and a sufficient light exposure time is set, in order to photograph a faint signal with high sensitivity and high accuracy. This method is effective for the case where the structure of a substance does not change, but is not suitable for measuring change in the structure of a substance.

Thus, an object of one embodiment of the present invention is to provide a transmission electron diffraction measurement apparatus which is capable of analyzing the structure between crystal regions in a substance. Another object of one embodiment of the present invention is to provide a transmission electron diffraction measurement apparatus which is capable of analyzing change in the structure of a substance. Another object of one embodiment of the present invention is to provide a transmission electron diffraction measurement apparatus which is capable of analyzing a two-dimensional structure of a substance. Another object of one embodiment of the present invention is to provide a transmission electron diffraction apparatus which is capable of analyzing a three-dimensional structure of a substance.

Another object of one embodiment of the present invention is to provide a method for measuring a transmission electron diffraction pattern using the transmission electron diffraction measurement apparatus.

Note that the descriptions of these objects do not disturb the existence of other objects. in one embodiment of the present invention, there is no need to achieve all the objects. Other objects will be apparent from and can be derived from the description of the specification, the drawings, the claims, and the like.

One embodiment of the present invention is a transmission electron diffraction measurement apparatus which is capable of taking a. transmission electron diffraction pattern appearing in an observation chamber with the use of a camera. Another embodiment of the present invention is a method for measuring a transmission electron diffraction pattern using the transmission electron diffraction measurement apparatus.

When an electron-beam probe diameter is less than or equal to 50 nm (an electron-beam emitted from a prove with such a probe diameter is referred to as a nanometer-sized electron beam), emitted light derived from a transmitted wave of a transmission electron diffraction pattern is too bright; therefore, another transmission electron diffraction pattern cannot be taken in some cases because the pattern is covered with the light derived from the transmitted wave of the transmission electron diffraction pattern. In addition, there is a case where burn-in occurs in an imaging sensor owing to the emitted light derived from a transmitted wave.

In the above manner, the use of a camera for taking a transmission electron diffraction pattern has not been adequately considered so far in terms of technical difficulty and demand. In particular, taking a moving image of a transmission electron diffraction pattern has been hardly considered so far.

However, since an In—Ga—Zn oxide film including CAAC was reported, the importance of taking a transmission electron diffraction pattern using a camera has been increasing. That is, there is a possibility that a novel crystal structure can be analyzed in detail by successively capturing changes in a transmission electron diffraction pattern.

Thus, one embodiment of the present invention is a transmission electron diffraction measurement apparatus including an electron gun; a first optical system under the electron gun; a sample chamber under the first optical system; a second optical system under the sample chamber; an observation chamber under the second optical system; and a camera. The observation chamber has a region where a fluorescent plate capable of emitting light by receiving energy from an electron is set. The camera is arranged so as to face the region.

Note that the camera is preferably capable of taking an image even under an illuminance of 0.002 lux or less. in addition, the camera preferably includes a CCD image sensor with a size of ¼ inches or more.

Note that the sample chamber may include a holder with a heating function. Alternatively, the sample chamber may include a nozzle capable of supplying a gas. Further alternatively, the sample chamber may include an ion gun.

Another embodiment of the present invention is a method for measuring a transmission electron diffraction pattern including the steps of irradiating a substance set in a sample chamber with an electron emitted from an electron gun through a first optical system; making the electron passing through the substance enter a region that emits light by receiving energy from the electron through a second optical system; and taking a pattern appearing in the region with a camera.

Note that a moving image is taken with the camera.

Note that the pattern may be taken with the camera while the substance is heated. Alternatively, the pattern may be taken with the camera while a film is deposited on the substance. Further alternatively, the pattern may be taken with the camera while the substance is etched. Further alternatively, the pattern may be taken with the camera while an irradiation position of the electron in the substance is changed.

A step of taking the pattern with the camera while changing an irradiation position of the electron in the substance and a step of depositing a film on the substance may be performed repeatedly. Alternatively, a step of taking the pattern with the camera while changing an irradiation position of the electron in the substance and a step of etching the substance may be performed repeatedly.

A transmission electron diffraction measurement apparatus which is capable of analyzing the structure between crystal regions in a substance can be provided. A transmission electron diffraction measurement apparatus which is capable of analyzing change in the structure of a substance can be provided. A transmission electron diffraction measurement apparatus which is capable of analyzing a two-dimensional structure of a substance can be provided. A transmission electron diffraction apparatus which is capable of analyzing a three-dimensional structure of a substance can be provided.

A method for measuring a transmission electron diffraction pattern using the transmission electron diffraction measurement apparatus can be provided.

BRIEF DESCRIPTION OF THE DRAWINGS

FIGS. 1A and 1B illustrate an example of a transmission electron diffraction measurement apparatus of one embodiment of the present invention.

FIGS. 4A1, 4A2, and 4A3 illustrate a method for measuring a transmission electron diffraction pattern of one embodiment of the present invention, and FIG. 4B shows a flow chart.

FIGS. 5A1, 5A2, and 5A3 illustrate a method for measuring a transmission electron diffraction pattern of one embodiment of the present invention, and FIG. 5B shows a flow chart.

FIGS. 6A1, 6A2, and 6A3 illustrate a method for measuring a transmission electron diffraction pattern of one embodiment of the present invention, and FIG. 6B shows a flow chart.

FIGS. 7A1 and 7A2 illustrate a method for measuring a transmission electron diffraction pattern of one embodiment of the present invention, and FIG. 7B shows a flow chart.

FIGS. 8A1, 8A2, and 8A3 illustrate a method for measuring a transmission electron diffraction pattern of one embodiment of the present invention, and FIG. 8B shows a flow chart.

FIGS. 9A1 and 9A2 illustrate a method for measuring a transmission electron diffraction pattern of one embodiment of the present invention, and FIG. 9B shows a flow chart.

DETAILED DESCRIPTION OF THE INVENTION

Figure 2A:
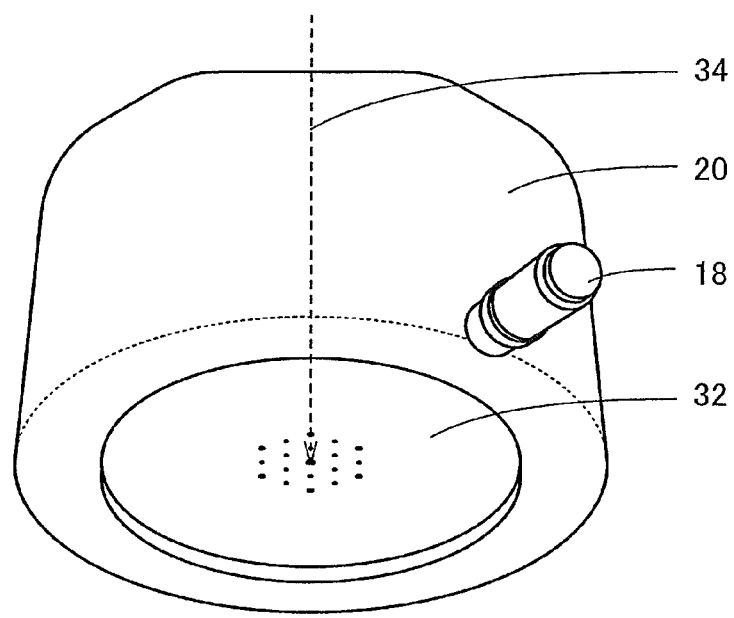
FIGS. 2A and 2B each illustrate an example of an observation chamber of a transmission electron diffraction measurement apparatus of one embodiment of the present invention.

Hereinafter, embodiments of the present invention will be described in detail with the reference to the drawings. However, the present invention is not limited to the description below, and it is easily understood by those skilled in the art that modes and details disclosed herein can be modified in various ways. Furthermore, the present invention is not construed as being limited to description of the embodiment and the example. in describing structures of the present invention with reference to the drawings, common reference numerals are used for the same portions in different drawings. Note that the same hatched pattern is applied to similar parts, and the similar parts are not especially denoted by reference numerals in some cases.

Note that what is described in one embodiment can be applied to, combined with, or exchanged with another content in the same embodiment and/or what is described in another embodiment or other embodiments.

Note that the size, the thickness of layers, or regions in diagrams is sometimes exaggerated for simplicity. Therefore, embodiments of the present invention are not limited to such a scale.

Note that the ordinal numbers such as "first" and "second" in this specification are used for the sake of convenience and do not denote the order of steps or the stacking order of layers. In addition, the ordinal numbers in this specification do not denote particular names which specify the present invention.

In this specification, for example, when the shape of an object is described with use of a term such as "diameter", "grain size (diameter)", "dimension", "size", or "width", the term can be regarded as the length of one side of a minimal cube where the object fits, or an equivalent circle diameter of a cross section of the object. The term "equivalent circle diameter of a cross section of the object" refers to the diameter of a perfect circle having the same area as that of the cross section of the object.

In this specification, a term "parallel" indicates that the angle formed between two straight lines is greater than or equal to −10° and less than or equal to 10°, and accordingly also includes the case where the angle is greater than or equal to −5° and less than or equal to 5°. In addition, a term "perpendicular" indicates that the angle formed between two straight lines is greater than or equal to 800 and less than or equal to 100°, and accordingly includes the case where the angle is greater than or equal to 85° and less than or equal to 95°.

This embodiment shows an example of a basic principle. Thus, part or the whole of this embodiment can be freely combined with, applied to, or replaced with part or the whole of another embodiment.

<Transmission Electron Diffraction Measurement Apparatus>

An example of a transmission electron diffraction measurement apparatus of one embodiment of the present invention is described below.

FIG. 1A illustrates a transmission electron diffraction measurement apparatus which includes an electron gun chamber 10, an optical system 12 under the electron gun chamber 10, a sample chamber 14 under the optical system 12, an optical system 16 under the sample chamber 14, an observation chamber 20 under the optical system 16, a camera 18 installed in the observation chamber 20, and a film chamber 22 under the observation chamber 20. The camera 18 is provided to face toward the inside of the observation chamber 20. Note that the film chamber 22 is not necessarily provided.

FIG. 1B illustrates an internal structure of the transmission electron diffraction measurement apparatus illustrated in FIG. 1A. In the transmission electron diffraction measurement apparatus, a substance 28 which is set in the sample chamber 14 is irradiated with electrons emitted from an electron gun installed in the electron gun chamber 10 through the optical system 12. The electrons passing through the substance 28 enter a fluorescent plate 32 provided in the observation chamber 20, through the optical system 16. On the fluorescent plate 32, a pattern corresponding to the intensity of entered electron appears, which allows measurement of a transmission electron diffraction pattern.

The camera 18 is installed so as to face the fluorescent plate 32 and can take a picture of a pattern appearing in the fluorescent plate 32. An angle which is formed by a line passing through the center of a lens of the camera 18 and the center of the fluorescent plate 32, and a line which passes through the center of the lens of the camera 18 and is perpendicular to a floor is, for example, greater than or equal to 15° and less than or equal to 80°, greater than or equal to 30° and less than or equal to 75°, or greater than or equal to 45° and less than or equal to 70°. As the angle is increased, distortion of the transmission electron diffraction pattern taken by the camera 18 becomes large. It is difficult to totally remove the distortion of the transmission electron diffraction pattern as long as the camera set outside the transmission electron diffraction measurement apparatus is used. This is one possible reason why a way to take a picture of a transmission electron diffraction pattern with a camera has not been considered for a long time. However, it is possible to correct the distortion of an obtained electron diffraction pattern if the angle is obtained in advance. Note that the film chamber 22 may be provided with the camera 18. For example, the camera 18 may be provided in the film chamber 22 so as to be opposite to the incident direction of electrons 24. In this case, a transmission electron diffraction pattern with less distortion can be taken from the rear surface of the fluorescent plate 32.

The camera 18 can store a taken image in a storage medium. For example, the camera 18 may be connected to a computer so that the computer displays a taken image. When an image is displayed by a computer, a noise which is peculiar to a highly sensitive photographing can be removed. Furthermore, it is possible to display a transmission electron diffraction pattern from which distortion derived from an inclination of the camera 18 is removed. in addition, it is possible to analyze change in the transmission electron diffraction pattern on the spot; therefore, a high effect for analyzing a novel crystal structure can be obtained.

As the camera 18, a high sensitive camera such as a camera for astronomical observation may be used, for example. As the camera 18, for example, a camera which can take an image even when the illuminance is lower than or equal to 0.002 lux, preferably lower than or equal to 0.001 lux, further preferably lower than or equal to 0.0005 lux, still further preferably lower than or equal to 0.0002 lux is used. As the camera 18, a camera which includes a charge-coupled device (CCD) image sensor with a size greater than or equal to ¼ inches, preferably greater than or equal to ⅓ inches, further preferably greater than or equal to 1/2.3 inches, still further preferably greater than or equal to ⅔ inches is used.

The camera 18 preferably has a backlight correction function, for example. A backlight correction function enables the camera to recognize a transmission electron diffraction pattern in some cases even when light derived from a transmitted wave of another transmission electron diffraction pattern is too bright. Furthermore, as the camera 18, it is preferable to use a camera in which burn-in due to light emission derived from a transmitted wave is less likely to occur.

The fluorescent plate 32 has a function of emitting light by receiving energy from electrons. Therefore, the fluorescent plate 32 is not limited to a plate to which a fluorescent material is applied as long as it has the above function, and can be replaced with a plate to which another illuminant is applied. For the fluorescent plate 32, a substance which emits light such as ultraviolet light, visible light (blue light, green light, red light, or the like), infrared light, or the like by receiving energy from electrons may be used.

Figure 2B:
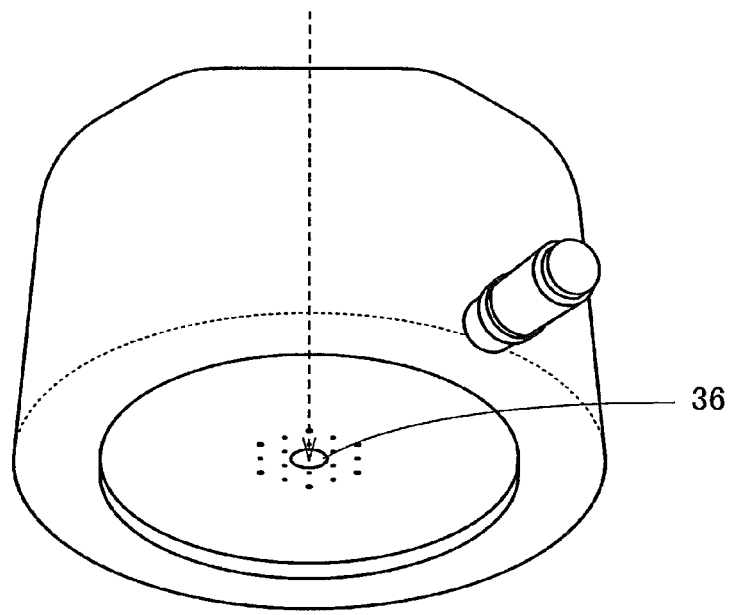

For example, depending on the shape or structure of the fluorescent plate 32, the fluorescent plate 32 may be the one that does not emit light having high intensity even by being irradiated with a transmitted wave. FIGS. 2A and 2B each illustrate the inside of the observation chamber 20. As illustrated in FIG. 2A, a transmitted wave 34 which enters the fluorescent plate 32 has a high tendency to travel in a straight line. Therefore, it is possible to make the transmitted wave 34 enter a predetermined region of the fluorescent plate 32. For example, the transmitted wave 34 enters a region near the center of the fluorescent plate 32. In this case, burn-in might occur in an imaging sensor of the camera 18 owing to the too bright light emission derived from the transmitted wave.

Thus, for example, the fluorescent plate 32 includes a region 36 as illustrated in FIG. 2B, whereby the intensity of the light emission derived from the transmitted wave can be reduced in some cases. For example, the region 36 may be a region having a small amount (a low density) of fluorescent material. Alternatively, the region 36 may be a region which does not include a fluorescent material. When the fluorescent plate 32 includes the region 36 in this manner, burn-in in the camera 18 can be prevented. in addition, a transmission electron diffraction pattern which is covered with intense light emission derived from the transmitted wave can be taken with high sensitivity.

Figure 3A:
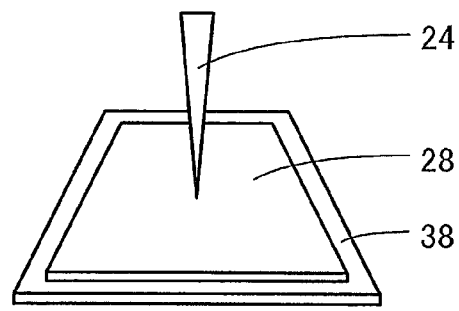
FIGS. 3A to 3C illustrate a method for measuring a transmission electron diffraction pattern of one embodiment of the present invention.

A holder 38 for fixing the substance 28 that is a sample is provided in the sample chamber 14 (see FIG. 3A). The holder 38 transmits electrons passing through the substance 28. The holder 38 may have a function of heating the substance 28, for example. Further, holder 38 may have a function of rotating the substance 28, for example. Furthermore, the holder 38 may have a function of moving the substance 28 in the direction of the x, y, and z axes, for example. The movement function of the holder 38 may have an accuracy of moving the substance 28 in the range of, for example, 1 nm to 10 nm, 5 nm to 50 nm, 10 nm to 100 nm, 50 nm to 500 nm, and 100 nm to 1 μm. The range is preferably determined to be an optimal range for the structure of the substance 28.

Figure 3B:
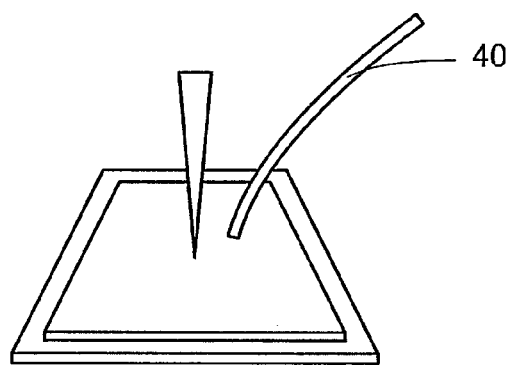

Alternatively, a nozzle 40 capable of supplying a gas may be provided in the sample chamber 14 (see FIG. 3B). Film deposition over the substance 28 or etching of the substance 28 may be possible by supply of a gas from the nozzle 40. For example, a film may be deposited in such a manner that the substance 28 is heated by the holder 38 while a. gas is supplied from the nozzle 40.

Figure 3C:
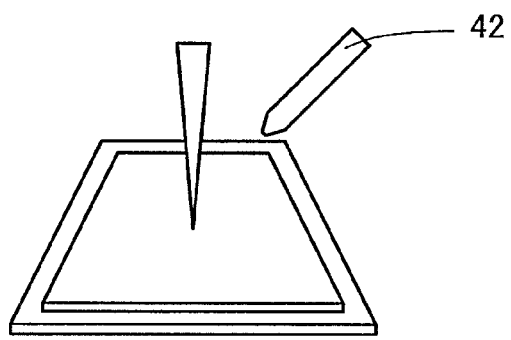

Furthermore, an ion gun 42 may be provided in the sample chamber 14 (see FIG. 3C). Film deposition over the substance 28 or etching of the substance 28 may be possible by irradiation of ions from the ion gun 42. For example, a film may be deposited in such a manner that irradiation with ions is performed from the ion gun 42 while a gas is supplied from the nozzle 40. Examples of ions which can be used from the irradiation from the ion gun 42 include helium, neon, argon, krypton, xenon, nitrogen, oxygen, carbon tetrafluoride, cesium, and gallium.

A focusing lens or the like may be used for the optical system 12. For example, the substance 28 in the sample chamber 14 may be irradiated with the electrons 24 which have passed through three or more kinds of focusing lenses and a focusing aperture, through an object lens.

An intermediate lens and a projector lens may be used for the optical system 16. For example, the electrons 24 which have passed through the substance 28 may pass through an object lens and three or more kinds of intermediate lenses to enter the fluorescent plate 32 of the observation chamber 20 through a projector lens.

A thermionic-emission electron gun or a field-emission electron gun can be used for the electron gun chamber 10. In particular, a field-emission electron gun is preferably used because it is capable of emitting a minute electron beam, which results in high current density. Tungsten (including an emitter of tungsten covered with zirconium oxide, and the like), $LaB_6$, or the like may be used as an emitter of the electron gun.

A film or an imaging plate can be set in the film chamber 22.

<Method for Measuring Transmission Electron Diffraction Pattern>

A method for measuring a transmission electron diffraction pattern of a substance is described using the above-described transmission electron diffraction measurement apparatus.

FIGS. 4A1 to 4B show a method for measuring a change in the structure of a substance.

FIGS. 4A1 to 4A3 show changes in a transmission electron diffraction pattern appearing on the fluorescent plate 32. FIG. 4B is a flow chart showing changes in the transmission electron diffraction pattern.

First, a ring-shaped transmission electron diffraction pattern shown in FIG. 4A1 is observed (see Step S1001 in FIG. 4B). The result at this point shows that the substance has no alignment in particular.

Here, for example, when the substance is continuously heated, a change in the structure of the substance can be observed. For example, as shown in FIG. 4A2, a transmission electron diffraction pattern in which bright spots overlap a ring is observed (see Step S102 in FIG. 4B). The result at this point indicates that the substance begins to have alignment gradually.

When the substance is further heated, for example, the ring disappears and a transmission electron diffraction pattern with bright spots is observed as shown in FIG. 4A3 (see Step S103 in FIG. 4B). The result at this point shows that the substance has alignment.

That is, the result as shown in FIGS. 4A1 to 4B shows that the substance is crystallized after being subjected to heat treatment for a predetermined time.

A relationship between heating time and change in the structure of a substance can be found by using such a method for measuring a transmission electron diffraction pattern. Therefore, a plurality of samples heated for different periods of time is not necessary. Accordingly, the experiment can be efficiently performed.

Next, FIGS. 5A1 to 5B show a measurement method for identifying a substance having a polycrystalline structure.

FIGS. 5A1 to 5A3 show changes in a transmission electron diffraction pattern appearing on the fluorescent plate 32. FIG. 5B is a flow chart showing changes in the transmission electron diffraction pattern.

First, a transmission electron diffraction pattern of bright spots shown in FIG. 5A1 (the bright spots are represented as Bright spots 1) is observed (see Step S111 in FIG. 5B).

Here, changes in the structure of a substance can be observed by changing an irradiation position of electrons in the substance. For example, as shown in FIG. 5A2, a transmission electron diffraction pattern in which two different kinds of bright spots (represented as Bright spots 1 and Bright spots 2) overlap with each other is observed (see Step S112 in FIG. 5B).

The irradiation position of electrons in the substance is further changed, whereby, for example, Bright spots 1 disappear and a transmission electron diffraction pattern with only Bright spots 2 is observed as shown in FIG. 5A3 (see Step S113 in FIG. 5B).

In other words, the result as shown in FIGS. 5A1 to 5B shows that the substance has a polycrystalline structure having crystal grain boundaries.

Next, FIGS. 6A1 to 6B show a measurement method for identifying a substance having a structure with CAAC (also referred to as a CAAC structure) using a method similar to that shown in FIGS. 5A1 to 5B.

FIGS. 6A1 to 6A3 show changes in a transmission electron diffraction pattern appearing on the fluorescent plate 32. FIG. 6B is a flow chart showing changes in the transmission electron diffraction pattern.

First, a transmission electron diffraction pattern of bright spots shown in FIG. 6A1 is observed (see Step S121 in FIG. 6B).

Here, changes in the structure of a substance can be observed by changing an irradiation position of electrons in the substance. For example, a situation where bright spots are rotated about the transmission wave is observed as shown in FIGS. 6A1 and 6A2. The irradiation position of electrons in the substance is further changed, whereby, for example, a situation where the bright spots are further rotated about the transmission wave is observed as shown in FIGS. 6A2 and 6A3 (see Step S122 in FIG. 6B). That is, FIGS. 6A1 to 6A2 and FIGS. 6A2 and 6A3 each show that the crystal orientation of the substance is rotated.

That is, such results as shown in FIGS. 6A1 to 6B show that the substance has a CAAC structure having no crystal grain boundary.

A change in one-dimensional structure of a substance can be found by using such a method for measuring a transmission electron diffraction pattern, so that it is possible to distinguish a novel crystal structure such as a CAAC structure from a polycrystalline structure.

<Application>

Measurement methods for analyzing the structure of a substance one-dimensionally, two-dimensionally, and three-dimensionally, which are application examples of the method for measuring a transmission electron diffraction pattern, are described below.

First, a method for measuring a transmission electron diffraction pattern for the purpose of one-dimensionally analyzing the structure of a substance is described with reference to FIGS. 7A1 to 7B.

FIG. 7A1 shows a positional relationship at the beginning of measurement among the holder 38, the substance 28 fixed to the holder 38, and the electrons 24 with which the substance 28 is irradiated. First, irradiation of electrons is started in the state of the positional relationship shown in FIG. 7A1 (at the start point of measurement) and a transmission electron diffraction pattern is measured (see Step S131 in FIG. 7B).

Next, as illustrated in FIG. 7A2, the holder 38 including the substance 28 is moved while the position of the electrons 24 is not changed. In this manner, measurement of a transmission electron diffraction pattern can be performed one-dimensionally by changing the irradiation position of the electrons 24 (see Step S132 in FIG. 7B). By observing a change in the transmission electron diffraction pattern, for example, structural change in the substance 28 may be seen as shown in FIGS. 4A1 to 4B, FIGS. 5A1 to 5B, and FIGS. 6A1 to 6B.

Next, a method for measuring a transmission electron diffraction pattern for two-dimensionally analyzing the structure of a substance is described with reference to FIGS. 8A1 to 8B.

FIG. 8A1 shows a positional relationship at the beginning of measurement among the holder 38, the substance 28 fixed to the holder 38, and the electrons 24 with which the substance 28 is irradiated. First, irradiation of the electrons is started in the state of the positional relationship shown in FIG. 8A1 (at the start point of measurement) and measurement of a transmission electron diffraction pattern is performed in a first direction by the measurement method shown in FIGS. 7A1 to 7B or the like (see Step S141 in FIG. 8B).

Next, whether the measurement of the transmission electron diffraction pattern is to be continued or finished is determined (see Step S142 in FIG. 8B). In the case where the measurement is to be finished, the measurement of a transmission electron diffraction pattern is finished. The finish time may be predetermined.

In the case where the measurement is to be continued, together with the holder 38, the substance 28 is moved in a second direction while the position of the electrons 24 is not changed (see Step S143 in FIG. 8B). The second direction is, for example, substantially perpendicular to the first direction. Note that before the substance 28 is moved in the second direction together with the holder 38, it may be moved in a direction opposite to the first direction by the distance of a portion which has been subjected to the measurement of the transmission electron diffraction pattern.

Next, the process returns to Step S141, and transmission electron diffraction patterns are measured one-dimensionally in the first direction by, for example, the measurement method shown in FIGS. 7A1 to 7B. Steps S141 to S143 are repeated until the measurement is finished, whereby transmission electron diffraction patterns can be measured two-dimensionally by changing the irradiation position of the electrons 24 in the substance 28. The measurement of the transmission electron diffraction pattern is conducted, for example, as shown by a trace in FIG. 8A2 or 8A3. The measurement of a change in the transmission electron diffraction pattern may make it possible to find a change in two-dimensional structure of the substance 28.

Next, a method for measuring a transmission electron diffraction pattern for three-dimensionally analyzing the structure of a substance is described with reference to FIGS. 9A1 to 9B.

FIG. 9A1 shows a positional relationship at the beginning of measurement among the holder 38, the substance 28 fixed to the holder 38, and the electrons 24 with which the substance 28 is irradiated. First, irradiation of the electrons is started in the state of the positional relationship shown in FIG. 9A1 (at the start point of measurement) and measurement of a transmission electron diffraction pattern is performed two-dimensionally by the measurement method shown in FIGS. 8A1 to 8B or the like (see FIG. 8A2 and Step S151 in FIG. 9B).

Next, whether the measurement of the transmission electron diffraction pattern is to be continued or finished is determined (see Step S152 in FIG. 9B). In the case where the measurement is to be finished, the measurement of a transmission electron diffraction pattern is finished. The finish time may be predetermined.

In the case where the measurement is to be continued, the substance 28 is processed (Step S153 in FIG. 9B). The process of the substance 28 may be deposition of a film, for example. Alternatively, the process of the substance 28 may be etching of the substance 28.

Next, the process returns to Step S151, and transmission electron diffraction patterns are measured two-dimensionally by, for example, the measurement method shown in FIGS. 8A1 to 8B. Steps S151 to S153 are repeated in this manner until the measurement is finished, whereby measurement of the transmission electron diffraction pattern can be performed three-dimensionally in the directions including the thickness direction of the substance 28. The measurement of a change in the transmission electron diffraction pattern may make it possible to find a change in three-dimensional structure of the substance 28.

The descriptions in this embodiment can be combined with each other as appropriate.

EXAMPLE 1

In this example, one-dimensional transmission electron diffraction patterns of a polycrystalline In—Ga—Zn oxide film and an In—Ga—Zn oxide film including CAAC were measured. Note that each sample was formed so that the thickness in a direction in which electrons pass through was 30 nm.

Figure 10A:
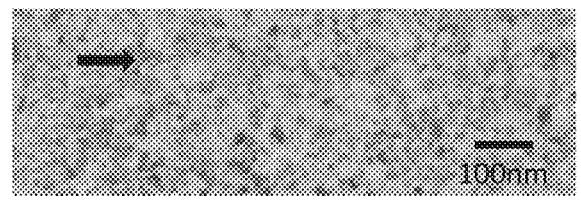
FIG. 10A shows a plan-view TEM image of a polycrystalline In—Ga—Zn oxide film and FIG. 10B shows change in the transmission electron diffraction pattern thereof.

FIG. 10A is a bright-field image of a plane of the polycrystalline In—Ga—Zn oxide film obtained with a transmission electron microscope (TEM) (such an image is also referred to as a plan-view TEM image). Here, the change in the transmission electron diffraction pattern was measured one-dimensionally in such a manner that the sample was moved in a direction shown by an arrow in the figure at approximately 10 nm/second. Note that the transmission electron diffraction pattern was measured using a Hitachi HF-2000 field-emission transmission electron microscope under conditions where the electron-beam probe diameter was 1 nm and the accelerating voltage was 200 kV. Although a film was not used in this example, a distance from the position of the sample to a position where the film is set in a film chamber (such a distance is referred to as a camera length) was 0.4 m.

Figure 10B:
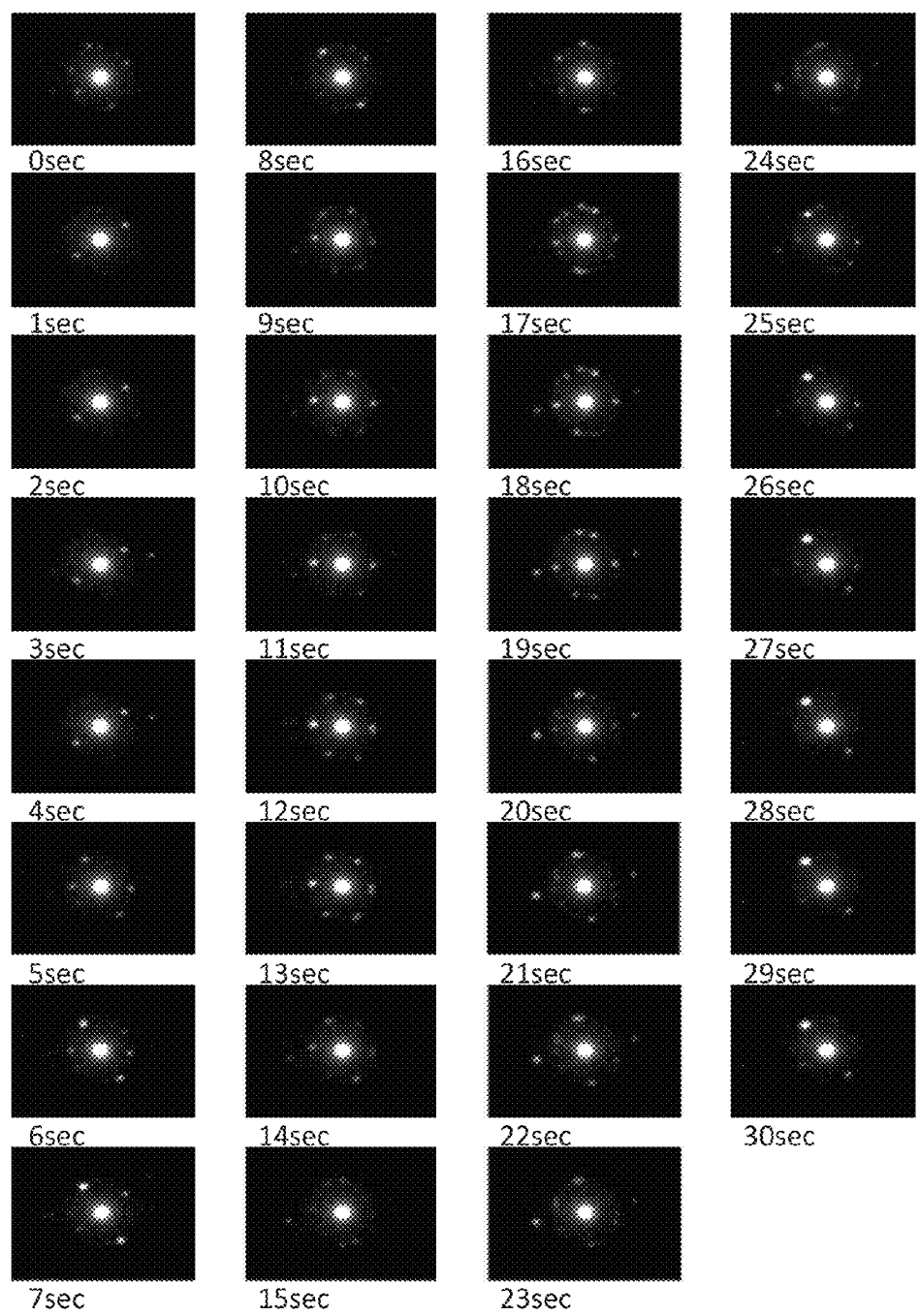

A moving image of the transmission electron diffraction pattern reflected on a fluorescent plate was taken using a monochrome camera WAT-902H3 ULTIMATE manufactured by Watec Co., Ltd. FIG. 10B shows transmission electron diffraction patterns from 0 seconds to 30 seconds at one-second intervals. As shown in FIG. 10B, transmission electron diffraction patterns in which two kinds of crystalline structure overlapped each other between crystal grains were observed in the polycrystalline In—Ga—Zn oxide film. That is, a structural connection between crystal grains was not shown.

Figure 11A:
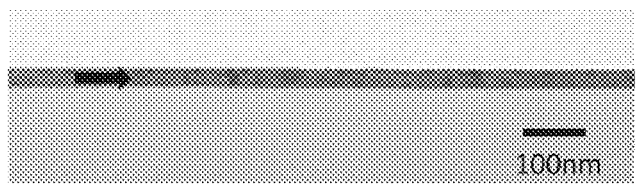
FIG. 11A shows a cross-sectional TEM image of a polycrystalline In—Ga—Zn oxide film and FIG. 11B shows change in the transmission electron diffraction pattern thereof.

In a similar manner, FIG. 11A is a bright-field image of a cross section of the polycrystalline In—Ga—Zn oxide film obtained by TEM (such an image is also referred to as a cross-sectional TEM image). Here, the changes in the transmission electron diffraction pattern were measured one-dimensionally in such a manner that the sample was moved in a direction shown by an arrow in the figure at approximately 10 nm/second.

Figure 11B:
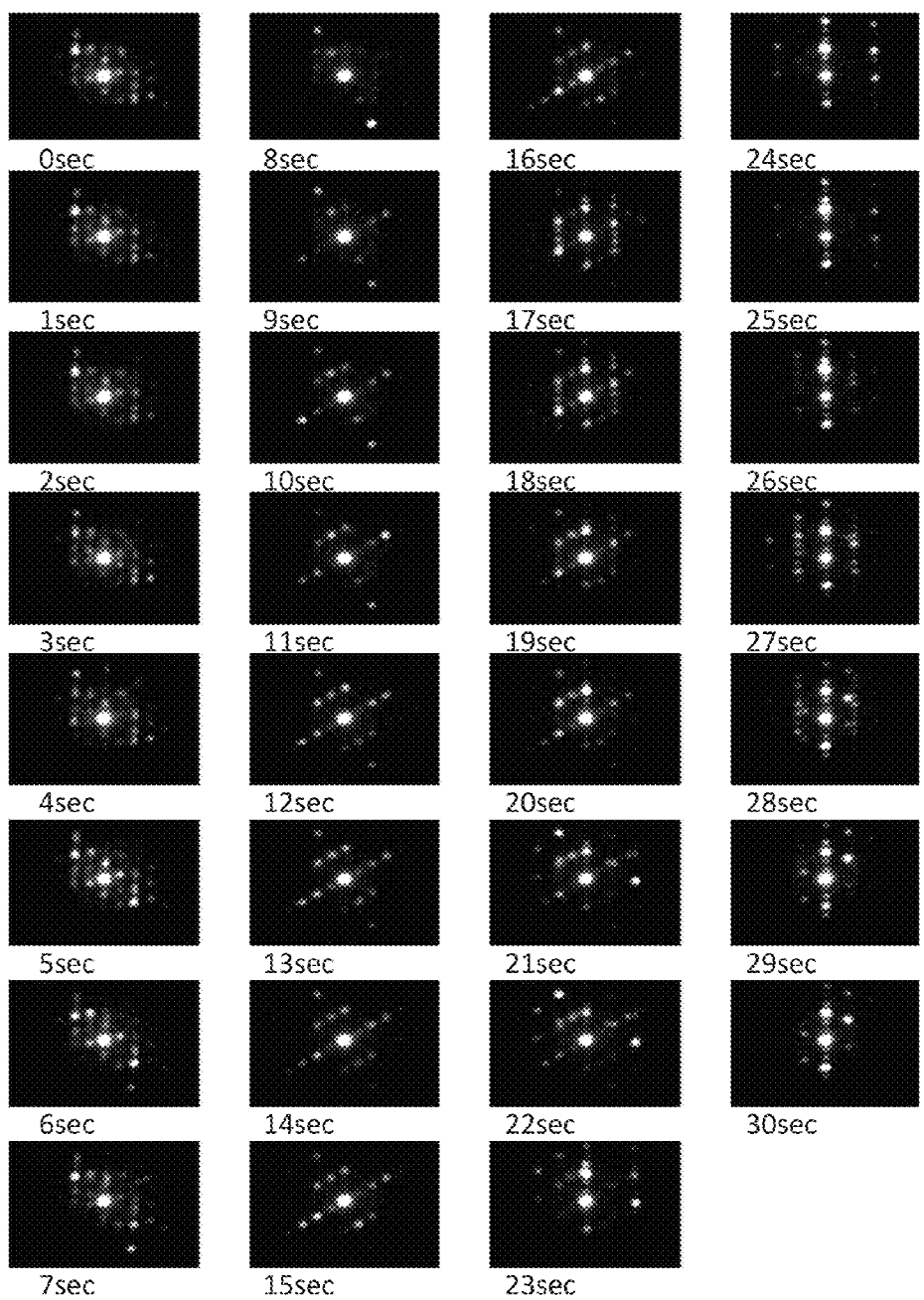

FIG. 11B shows transmission electron diffraction patterns from 0 seconds to 30 seconds at one-second intervals. As shown in FIG. 11B, transmission electron diffraction patterns in which two kinds of crystalline structure overlapped each other between crystal grains were observed in the polycrystalline In—Ga—Zn oxide film. That is, a structural connection between crystal grains was not shown.

By the method for measuring a. transmission electron diffraction pattern is used in the above manner, the one-dimensional structure of the polycrystalline In—Ga—Zn oxide film was analyzed.

Next, similar structural analysis was performed on the In—Ga—Zn oxide film having CAAC.

Figure 12A:
FIG. 12A shows a plan-view TEM image of an In—Ga—Zn oxide film including CAAC and FIG. 12B shows change in the transmission electron diffraction pattern thereof.

FIG. 12A is a plan-view TEM image of the In—Ga—Zn oxide film including CAAC. Here, the change in transmission electron diffraction pattern was measured one-dimensionally in such a manner that the sample was moved in a direction shown by an arrow in the figure at approximately 10 nm/second.

Figure 12B:
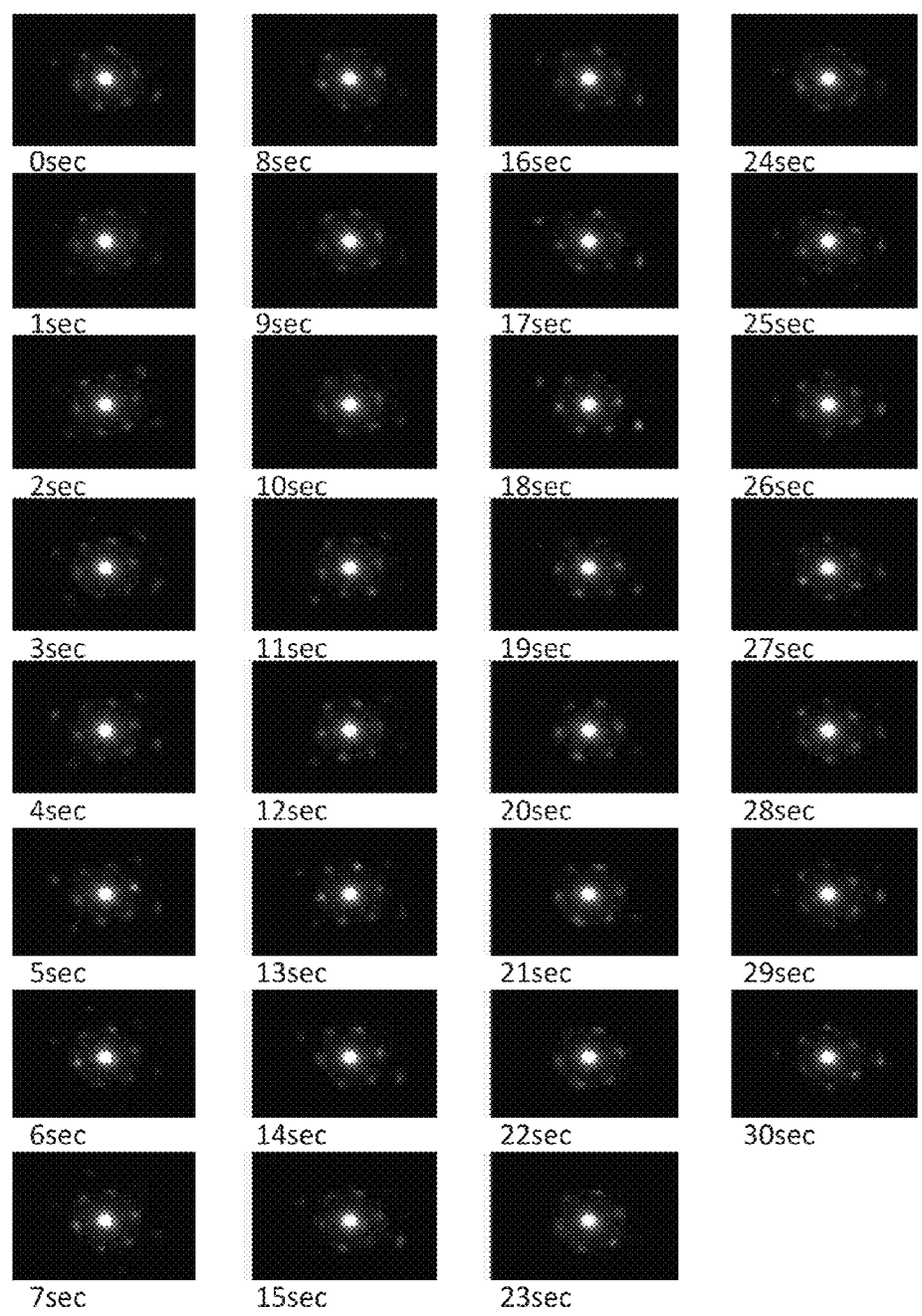

FIG. 12B shows transmission electron diffraction patterns from 0 seconds to 30 seconds at one-second intervals. As shown in FIG. 12B, transmission electron diffraction patterns which show that the structure is gradually changed between crystal regions are observed in the In—Ga—Zn oxide film including CAAC. This indicates the connection of the structures between the crystal regions.

Figure 13A:
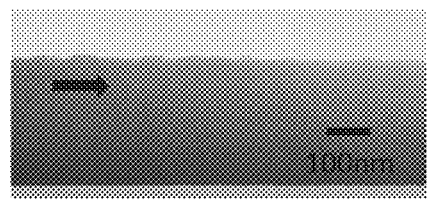
FIG. 13A shows a cross-sectional TEM image of an In—Ga—Zn oxide film including CAAC and FIG. 13B shows change in the transmission electron diffraction pattern thereof.

In a similar manner, FIG. 13A shows a cross-sectional TEM image of the In—Ga—Zn oxide film including CAAC. Here, the change in the transmission electron diffraction pattern was measured one-dimensionally in such a manner that the sample was moved in a direction shown by an arrow in the figure at approximately 10 nm/second.

Figure 13B:
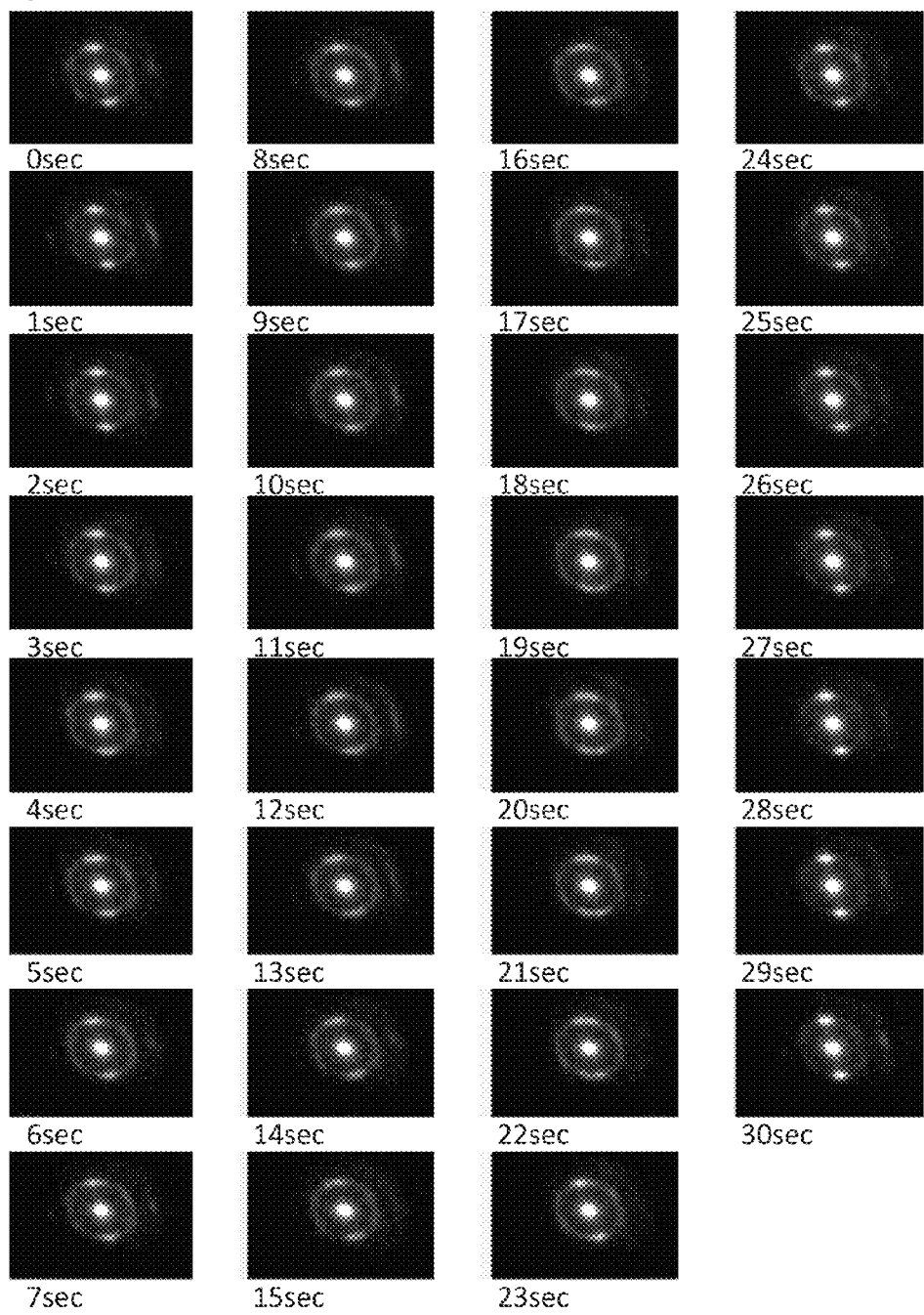

FIG. 13B shows transmission electron diffraction patterns from 0 seconds to 30 seconds at one-second intervals. As shown in FIG. 13B. it turned out that in the whole In—Ga—Zn oxide film including CAAC, the c-axis is oriented in a direction substantially perpendicular to the sample surface. In addition, transmission electron diffraction patterns showing that the c-axis direction is gradually changed along a finely uneven sample surface were obtained. In other words, the patterns indicate the connection of structures between crystal regions.

Thus, the method for measuring a transmission electron diffraction pattern enables one-dimension structural analysis of the In—Ga—Zn oxide film including CAAC. It was found that the In—Ga—Zn oxide film including CAAC has a different structure from the polycrystalline In—Ga—Zn oxide film.

As described in this example, it is possible to one-dimensionally measure a transmission electron diffraction pattern according to one embodiment of the present invention. In addition, it is possible to measure change in the structure between small regions. In particular, the method is effective to analyze a novel structure such as the structure of the In—Ga—Zn oxide film including CAAC. Furthermore, application of this example enables two-dimensional and three-dimensional measurements of transmission electron diffraction patterns.

This application is based on Japanese Patent Application serial no. 2013-141217 filed with Japan Patent Office on Jul. 5, 2013, the entire contents of which are hereby incorporated by reference.

What is claimed is:

1. A method for measuring a transmission electron diffraction pattern comprising the steps of:
   irradiating an oxide semiconductor film with an electron emitted from an electron gun; and
   taking a moving image of a pattern appearing on a fluorescent plate by irradiating the oxide semiconductor film with the electron,
   wherein the oxide semiconductor film includes indium, gallium, and zinc.

2. The method according to claim 1,
   wherein the fluorescent plate faces the electron gun with the oxide semiconductor film interposed therebetween,
   wherein the fluorescent plate is set in an observation chamber, and
   wherein the moving image is taken with a camera provided on a sidewall of the observation chamber and arranged so as to face the fluorescent plate.

3. The method according to claim 1, wherein the oxide semiconductor film is heated while the moving image is taken.

4. The method according to claim 1, wherein a film is deposited on the oxide semiconductor film while the moving image is taken.

5. The method according to claim 1, wherein the oxide semiconductor film is etched while the moving image is taken.

6. The method according to claim 1, wherein an irradiation position of the electron on the oxide semiconductor film is changed while the moving image is taken.

7. The method according to claim 1, wherein a step of changing an irradiation position of the electron on the oxide semiconductor film while the moving image is taken and a step of depositing a film on the oxide semiconductor film after changing the irradiation position are performed repeatedly.

8. The method according to claim 1, wherein a step of changing an irradiation position of the electron on the oxide semiconductor film while the moving image is taken and a step of etching the oxide semiconductor film after changing the irradiation position are performed repeatedly.

9. A method for measuring a transmission electron diffraction pattern comprising the steps of:
   irradiating an oxide semiconductor film with an electron emitted from an electron gun; and
   taking a moving image of a pattern appearing on a fluorescent plate by irradiating the oxide semiconductor film with the electron,
   wherein the oxide semiconductor film includes a c-axis aligned crystal.

10. The method according to claim 9,
   wherein the fluorescent plate faces the electron gun with the oxide semiconductor film interposed therebetween,
   wherein the fluorescent plate is set in an observation chamber, and
   wherein the moving image is taken with a camera provided on a sidewall of the observation chamber and arranged so as to face the fluorescent plate.

11. The method according to claim 9, wherein the oxide semiconductor film is heated while the moving image is taken.

12. The method according to claim 9, wherein a film is deposited on the oxide semiconductor film while the moving image is taken.

13. The method according to claim 9, wherein the oxide semiconductor film is etched while the moving image is taken.

14. The method according to claim 9, wherein an irradiation position of the electron on the oxide semiconductor film is changed while the moving image is taken.

15. The method according to claim 9, wherein a step of changing an irradiation position of the electron on the oxide semiconductor film while the moving image is taken and a step of depositing a film on the oxide semiconductor film after changing the irradiation position are performed repeatedly.

16. The method according to claim 9, wherein a step of changing an irradiation position of the electron on the oxide semiconductor film while the moving image is taken and a step of etching the oxide semiconductor film after changing the irradiation position are performed repeatedly.

17. A method for measuring a transmission electron diffraction pattern comprising the steps of:
   irradiating an oxide semiconductor film with an electron emitted from an electron gun; and
   taking a moving image of a pattern appearing on a fluorescent plate by irradiating the oxide semiconductor film with the electron while an irradiation position of the electron on the oxide semiconductor film is changed,
   wherein bright spots are rotated about the transmission wave in the moving image.

18. The method according to claim 17,
   wherein the fluorescent plate faces the electron gun with the oxide semiconductor film interposed therebetween,
   wherein the fluorescent plate is set in an observation chamber, and
   wherein the moving image is taken with a camera provided on a sidewall of the observation chamber and arranged so as to face the fluorescent plate.

* * * * *